United States Patent [19]

Walling et al.

[11] 3,956,404

[45] May 11, 1976

[54] PROCESS FOR PREPARING CYCLOALIPHATIC MONOTERPENIC ALCOHOLS

[75] Inventors: Cheves T. Walling, Salt Lake City, Utah; Chester R. Willis, Maple Shade, N.J.

[73] Assignee: Lever Brothers Company, New York, N.Y.

[22] Filed: Mar. 7, 1974

[21] Appl. No.: 449,147

Related U.S. Application Data

[63] Continuation of Ser. No. 164,440, July 20, 1971, abandoned.

[52] U.S. Cl. .................. 260/631.5; 260/476 C; 260/476 R; 260/489
[51] Int. Cl.² ................ C07C 33/05; C07C 35/18
[58] Field of Search ......... 260/631.5, 476 R, 476 C, 260/489

[56] References Cited
UNITED STATES PATENTS

| | | | |
|---|---|---|---|
| 2,762,838 | 9/1956 | Toland | 260/476 R |
| 3,210,402 | 10/1965 | Kochi | 260/476 R |

FOREIGN PATENTS OR APPLICATIONS

| | | | |
|---|---|---|---|
| 43-699 | 1968 | Japan | 260/631.5 |

OTHER PUBLICATIONS

Kochi "J. Am. Chem. Soc.," Vol. 84, pp. 1572–1579 (1962).
Matsubara, J. Chem. Soc. Japan, Vol. 75, pp. 894–896 (1954).
Monsuy, "Doctorial Thesis" Paris 1972 CNRS No. A05077 pp. 94–102, available to public Dec. 23, 1950.

*Primary Examiner*—Alton D. Rollins
*Assistant Examiner*—D. B. Springer
*Attorney, Agent, or Firm*—James J. Farrell; Kenneth F. Dusyn; Melvin H. Kurtz

[57] ABSTRACT

A process for preparing trans-carveol and perillyl alcohol comprising the oxidation respectively of alpha-pinene and beta-pinene by benzoyl peroxide using a catalyst comprising cuprous/cupric ions, to form the respective benzoate esters, followed by hydrolysis and purification of the resulting alcohols.

5 Claims, No Drawings

PROCESS FOR PREPARING CYCLOALIPHATIC MONOTERPENIC ALCOHOLS

This is a continuation of application Ser. No. 164,440, filed July 20, 1971, and now abandoned.

BACKGROUND OF THE INVENTION

1. Field of the Invention

The present invention relates to a process wherein beta-pinene is converted to perillyl alcohol and alpha-pinene is converted to trans-carveol.

The conversion process steps are substantially identical for both products. The process comprises the addition of benzoyl peroxide to beta-pinene or to alpha-pinene, catalyzed by cuprous ion, to form respectively perillyl benzoate or carveyl benzoate, followed by alkaline hydrolysis to form the respective alcohols. Yields are good, usually from about 60% to about 77%, based on benzoyl peroxide and a 2:1 to 5:1 ratio of pinene to benzoyl peroxide.

The instant invention resulted from experimental efforts to develop a process to meet the need for a less expensive perillyl alcohol and carveol for use in perfume blends. Prior to the present invention the high cost of these alcohols prohibited their use in any but the most expensive perfumes, and advantage could not be taken of their valuable odor, which makes them important as a lavandin extender in perfume blends suitable for soaps and detergent compositions.

2. The Prior Art

As early as Mar. 7, 1911 the art was apprised of the utility of pinene as a starting material for the production of another perfume substance with the issuance of U.S. Pat. No. 986,038, which describes the conversion of pinene to borneol.

U.S. Pat. No. 2,340,294, which issued on Feb. 1, 1944 relates to the reaction of beta-pinene with formaldehyde to form a dicyclic primary alcohol.

Processes for making perillyl alcohol and carveol have been known, but those processes have provided relatively poor yields, i.e., not over about 45%. For example there is described in Chem. Abs. 68, 87418t (1968), referring to British Pat. No. 1,094,875, a process wherein beta-pinene is oxidized by lead compounds in the presence of a fatty acid dissolved in glacial acetic acid to perillyl acetate, which is hydrolyzed to perillyl alcohol. The yield in this reaction is 45%.

Similarly reference is made to Chem. Abs. 63, 4335f (1965) and Chem. Abs. 64, 9776b (1966) wherein beta-pinene is oxidized with $Pb_3O_4$ in glacial acetic acid to form perillyl alcohol.

Japanese Pat. No. 20,177 describes the synthesis of perillyl alcohol involving oxidation by lead tetraacetate. Yield is 45% based on beta-pinene.

The oxidation reaction with benzoyl peroxide is known as applied to the lower molecular weight olefins. For example J. K. Kochi, in J. Am. Chem. Soc. 84, 1572 (1962) describes a process of reacting butene-1 and butene-2 with benzoyl peroxide, in the presence of cuprous halides and cupric benzoate, at about 65° to 75°C for 24 hours. The conversion of butene-1 and butene-2 to $C_4$ benzoates by the reaction described by Kochi involves a carbon-hydrogen homolytic cleavage.

SUMMARY OF THE INVENTION

It has now been discovered that perillyl alcohol and trans-carveol can be prepared from the hydrocarbons beta- and alpha-pinene respectively in higher yields than heretofore by a process involving the free-radical addition of benzoyl peroxide to these hydrocarbons, catalyzed by cuprous ion, followed by alkaline hydrolysis.

Accordingly it is an object of the present invention to provide a process for making trans-carveol and perillyl alcohol in improved yields.

It is a further object of the invention to provide a process wherein alpha-pinene and beta-pinene are treated with benzoyl peroxide in the presence of cuprous ions, to form the respective benzoates, followed by alkaline hydrolysis to produce trans-carveol and perillyl alcohol respectively.

In its broadest aspect the invention provides a process for the preparation of cycloaliphatic monoterpenic alcohol selected from the group consisting of trans-carveol and perillyl alcohol comprising oxidizing a pinene isomer selected from the group consisting of alpha-pinene and beta-pinene with benzoyl peroxide in a free-radical reaction catalyzed by cuprous ions to form a benzoate ester of said alcohol, and subsequently hydrolyzing said ester in an alkaline medium to form said alcohol.

In another aspect, the invention provides a process for preparing trans-carveol and perillyl alcohol from isomeric pinenes, in the presence of a catalytic mixture of cuprous and cupric ions, comprising oxidizing said pinene with benzoyl peroxide in a polar organic solvent at about 50°–75°C, the pinene being in molar excess in relation to the peroxide, separating the thus-formed benzoate ester, and hydrolyzing in an alkaline aqueous alcoholic medium, steam distilling, and recovering the trans-carveol or perillyl alcohol. The cupric ion, or compound, is present in an amount at least sufficient to minimize polymerization of the pinene.

To reduce the hazards involved in the handling of benzoyl peroxide, it may be added in increments over a period of time up to about 10 hours or longer, for example one-eighth of the peroxide may be added hourly for a period of 8 hours. The incremental addition of peroxide does not affect the yield as compared with the yield obtained when all of the peroxide is added at one time. Accordingly the instant process contemplates the incremental addition of benzoyl peroxide over a predetermined length of time.

It is also an embodiment of the present invention that advantage be taken of the excellent perfumery qualities of the alcohols resulting from the process of the invention by incorporating these alcohols into a perfume blend, as set forth hereinafter. The alcohols may be used in perfume blends to impart thereto their distinctive notes, or may be blended with other perfume ingredients to enhance similar olfactory qualities thereof. For example perillyl alcohol may be blended at about 0.5 percent by weight to about 30 percent by weight with other perfume ingredients to impart a lavandin note thereto, (or may be used as a lavandin extender either with lavandin alone or in a blend containing lavandin). When used with lavandin, the percentage by weight of perillyl alcohol may range from about 0.5 percent by weight to about 10 percent by weight, based on the total blend, or from 0.5 percent by weight to 40 percent by weight based on the total of lavandin and extender.

Similarly trans-carveol may be blended at about 0.5 percent by weight to about 30 percent by weight with other perfume ingredients to impart a herbaceous, camphoraceous, earthy note thereto, or may be used in a perfume blend at about 0.5 percent by weight to about 10 percent by weight in conjunction with lavandin oil to accentuate the character thereof.

As in the case of perillyl alcohol, trans-carveol may be blended with lavandin as an extender therefor. The extender then, may be a member selected from the group consisting of perillyl alcohol and trans-carveol, and may be present with lavandin in the proportions of about 0.5% to about 40% by weight, based on the total of lavandin and extender. The mixture of lavandin and extender, whether or not premixed, may be blended with other perfume ingredients in the proportions of about 10% to about 50%, based on the weight of the total blend, the proportions being selected to provide about 0.5% to about 10% of extender, total blend basis, and sufficient to enhance the lavandin note of the blend.

By the expression "catalytic amount", when referring to the cuprous catalyst, is meant an amount at least sufficient to catalyze the described reaction. The permissible proportions of cuprous catalyst may vary over a wide range, for example from about 0.05 gram to about 5 grams per 100 ml of solvent. A preferred range is about 0.1 gram to about 2 grams per 100 ml of solvent. Typically about 0.15 gram of a cuprous halide per 100 ml of solvent has an effective catalytic action.

Among the catalysts that may be used are CuCl, CuBr, FeBr$_2$ and FeCl$_2$.

By the expression "an amount at least sufficient to minimize polymerization of the pinene" as applied to the cupric compound, it is expressly indicated that the proportion of cupric compound must be sufficiently high so that enough is present to direct the reaction to the greatest possible extent toward the desired product with a minimum of polymer formation in side reactions. The proportions of cupric compound may vary from about 0.5 gram to about 10 grams per 100 ml of solvent. Preferred amounts are from about 0.7 to about 5 grams of cupric compound per 100 ml of solvent. A satisfactory level of cupric benzoate is about 1 gram per 100 ml of solvent. Among the compounds that may be used to minimize polymerization there may be mentioned cupric benzoate, cupric acetate, ferric benzoate and ferric acetate.

Perillyl alcohol, or 4-isopropenyl-1-cyclohexenecarbinol, molecular weight 152.23, occurs naturally in a number of essential oils, such as gingergrass, bergamot, savin, and lavandin oils. It is rather viscous and its odor is reminiscent of that of linalool and terpineol.

Trans-carveol, or 1-methyl-4-isopropenyl-6-cyclohexen-2ol, molecular weight 152.23, is isomeric with perillyl alcohol. It occurs naturally in small quantities in caraway seed oil. It is a colorless oil resembling terpineol in odor.

The chemical structures, physical characteristics, etc. of trans-carveol and perillyl alcohol, and the compositions of oils in which these alcohols naturally occur, may be found in the six-volume treatise "The Essential Oils", Guenther, 1949, D. Van Nostrand Compound, Inc., New York.

The perillyl alcohol of the present invention is useful as a perfume ingredient to extend the usefulness of lavandin oil in perfume blends. Lavandin oil is obtained from plants that are a hybrid between true lavender and spike lavender. The oil is composed of a variety of aromatic constituents, including 1-perillyl alcohol.

Carveol finds utility as a perfume ingredient.

The molecular structure of alpha- and beta-pinene may be depicted as follows:

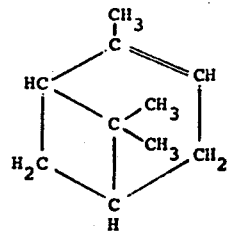 or 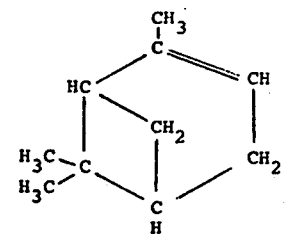

beta-pinene

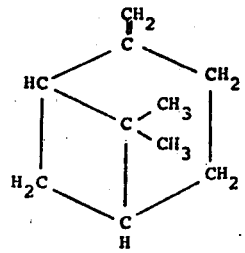 or 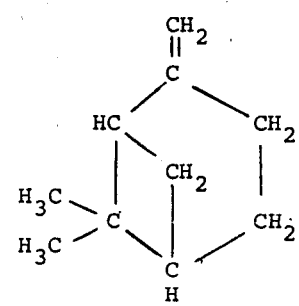

The molecular structures of trans-carveol and perillyl alcohol may be represented as:

trans-carveol            perillyl alcohol

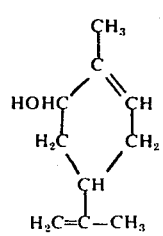   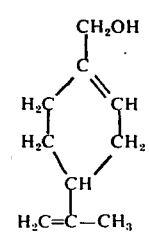

The reactions for the conversion of alpha-pinene to trans-carveol may be represented as follows:

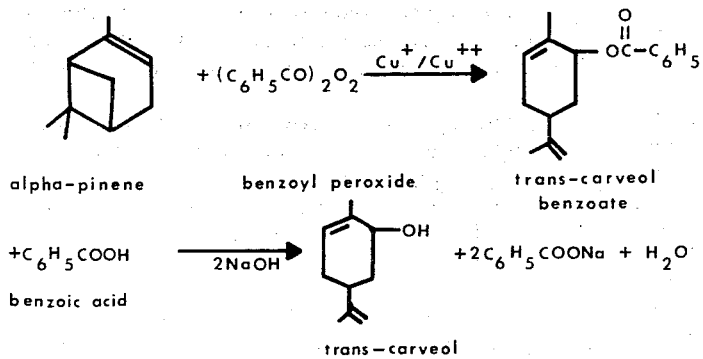

The reactions for the conversion of beta-pinene to perillyl alcohol may be represented as follows:

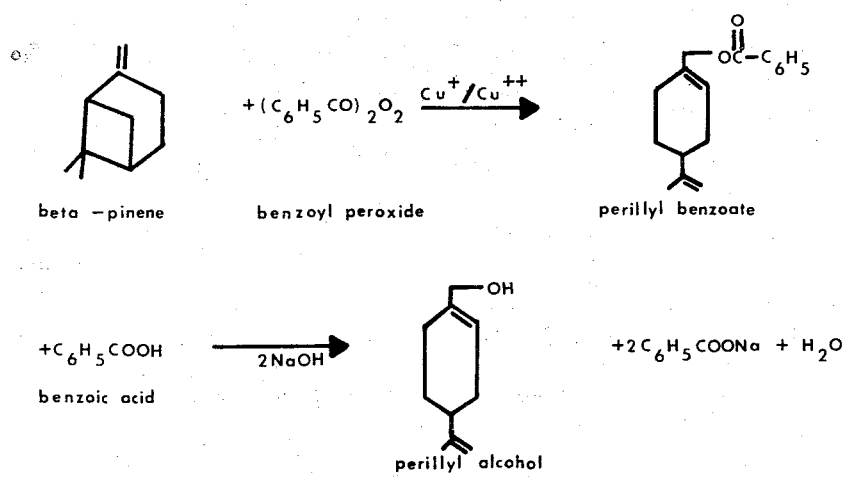

The reaction as set forth in the above schemes is carried out in a polar solvent medium, suitably acetonitrile or a 1:1 benzene : acetic acid mixture.

The solvent system must be polar. If the non-polar beta-pinene is used in excess as the solvent, the reaction products are only polymeric substances. For reasons not apparent, if the solvent is glacial acetic acid alone, a completely polar solvent system, perillyl alcohol is obtained in only about a 40% yield.

Cuprous ion is introduced into the reaction mixture as a catalyst. In addition, if cupric ion is also present, the reaction is directed toward the formation of the desired alcohols, rather than toward polymerization by attack on the beta-pinene.

It is preferred that the benzoyl peroxide be pure, although good yields are obtained when the commercial peroxide containing 30% water is used. For example a yield of 61.2% perillyl alcohol based on benzoyl peroxide is obtained in acetonitrile when the benzoyl peroxide used is the abovedescribed commercial material.

The reaction is carried out at elevated temperatures, suitably at 65° ± 5°C, although this may vary over the range of about 50°C to about 75°C, and if desired the reaction may be carried out at temperatures as low as about 40°C up to as high as about 85°C.

The yield of perillyl alcohol or trans-carveol produced by the instant process is influenced by the molar ratio of pinene to benzoyl peroxide. A moderately good yield is obtained at a 1:1 molar ratio, but yields are improved when the pinene reactant is in molar excess of the benzoyl peroxide. For example yields are greatly improved when the molar ratio is about 2:1, with a general trend toward greater yields as the molar ratio is increased, particularly when the solvent is a mixture of equal volumes of benzene and acetic acid. The influence of molar ratios of pinene to benzoyl peroxide on yield is evident from Table II, presented hereinbelow. Thus useful molar ratios of pinene to benzoyl peroxide are at least 1:1, and specifically 1:1 to about 5:1. The preferred range is about 2:1 to about 5:1, this being the range within which high yields are obtained, as illustrated in the aforementioned Table II. The use of pinene and benzoyl peroxide in a molar ratio of above 5:1 results in particularly good yields. It is preferred that the pinene be in molar excess, for example about 1.03 to 1 with respect to the benzoyl peroxide, as exemplified in Example 2.

In accordance with the instant process, a free-radical reaction takes place whereby carbon-carbon cleavage occurs with oxidation and rearrangement to form benzoate esters, very little, probably less than 2%, acetate esters being formed.

The reaction takes place by heating at temperatures and for lengths of time set forth elsewhere in this application. In the reaction the benzoyl peroxide is substantially consumed, and the medium after the reaction comprises benzoate esters, benzoic acid, and unreacted pinene. The polar solvent and unreacted pinene are removed by evaporation, preferably at subatmospheric pressure. The crude esters are recovered by addng ether to the residue remaining, filtering to remove insoluble copper compounds, and evaporating the ether. The residue from the ether evaporation contains benzoate esters. The esters are hydroylzed in an alkaline alcoholic medium to form the desired alcohols, namely perillyl alcohol or trans-carveol. The alcohol comprising the aforesaid alcoholic medium is preferably methanol, by any low molecular weight monohydric alcohol or polyhydric alcohol or glycol may be used. Methanol is preferred because it is most readily removed from the system, although ethyl, n-propyl, or isopropyl alcohols may be used. Also useful, if it is not desired to remove the alcohol from the system, are glycerol, dioxane, ethylene, glycol, propylene glycol, diethylene glycol, the low molecular weight (e.g., 1 to 4 carbon chain lengths) alkyl ethers of the aforementioned glycols, etc.

The alkalinity may be furnished by any alkaline substance suitable for cleaving the ester linkage. Sodium hydroxide is preferred, although other akali metal hydroxides are useful, sudh as potassium hydroxide and lithium hydroxide. Tetramethyl ammonium hydroxide may also be used.

After hydrolyzing the esters to form the corresponding alcohols, the low molecular weight alcohol solvent is removed and the residue steam-distilled to form a distillate containing the desired monoterpenic alcohols. The monoterpenic alcohols are extracted from the distillate with ethyl ether, and recovered by evaporation of the ether.

The invention will be more fully understood by reference to the following Examples, which are presented for illustrative purposes, and are not to be interpreted as limiting the scope of the invention.

EXAMPLE 1

Trans-carveol may be prepared as follows:

A well stirred solution of benzoyl peroxide (24.0 g), cuprous chloride (0.2 g), cupric benzoate (1.5 g) and alpha-pinene (28.0 g) in acetonitrile (150 ml) is heated on an oil bath at 65° ± 5° for 24 hours. The acetonitrile is removed by evaporation under vacuum (water pressure) at 40°. Excess alpha-pinene is recovered by continuing the evaporation at 75° (3 mm). The resulting blue-green slurry is dissolved in 100 ml ether and the solution filtered to remove the cupric benzoate. The filtrate is washed with 2N HCl (2 × 30 ml), distilled water (3 × 30 ml) and then the ether removed by evaporation. This gives a straw colored oil which is dissolved in a solution of methanol (200 ml), water (50 ml), NaOH (10 g), and hydroylzed by refluxing 1 hour. Removal of the methanol affords an aqueous suspension which is diluted with water (100 ml) and steam distilled. The distillate is extracted with ether (4 × 20 ml). This organic solution is dried over magnesium sulphate and evaporated to yield crude trans-carveol (9.2 g). Distillation affords pure material, b.p. 106°–110°C (10 mm).

The final product is identified as trans-carveol by boiling point, refractive index, and by nuclear magnetic reasonance (nmr), and gas-liquid chromatographic (glc) techniques, as set forth below.

The boiling point of the product is 106°–110°C at 10 mm (literature 108°C at 116 mm). The refractive index at 20°C is 1.49617 (literature 1.4956).

The nmr data are obtained on a Varian A-60 instrument, the graph showing the following characteristics:

The glc data are obtained on an Aerograph 1520 unit. The product is passed through a 6-foot helical column containing 2% Carbowax uniformly distributed on 80–100 mesh Chromasorb waw, at a temperature of 90°C and at a controlled flow rate of 50 ml per minute. Under these conditions, the retention time is 2.8 minutes.

The literature values referred to in Examples 1 and 2 are found in the "Dictionary of Organic Compounds", Oxford University Press, New York, 1965.

The refractive index masurements are made on a Valentine Technical Refractometer.

EXAMPLE 2

Perillyl alcohol may be prepared as follows. In this procedure the solvent is acetonitrile, and the catalyst is a mixture of cuprous chloride and cupric benzoate. The molar ratio of beta-pinene to benzoyl peroxide is 1.03 to 1.

A well stirred solution of benzoyl peroxide (24.2 g, 0.1 mole) cuprous chloride (0.2 g), cupric benzoate (1.5 g) and beta-pinene (14 g. 0.103 mole) in acetonitrile (150 ml) is heated on an oil bath at 65° ± 5° for 24 hours. The acetonitrile is removed by evaporation under vacuum (water pressure) at 40°. Excess beta-pinene is then recovered by continuing the evaporation at 75° (3 mm). The resulting blue-green slurry is dissolved in 100 ml ether and the solution filered to remove the cupric benzoate. The filtrate is washed with 2N HCl (2 × 30 ml), distilled water (3 × 30 ml) and then the ether removed by evaporation. This gives a straw colored oil which is dissolved in a solution of methanol (200 ml), water (50 ml), NaOH (10 g), and hydrolyzed by refluxing for 1 hour. Removal of methanol affords an aqueous suspension which is diluted with water (100 ml) and steam distilled. The distillate (1L) is extracted with ether (4 × 200 ml). This organic solution is dried over magnesium sulphate and evaporated to yield perillyl alcohol.

The final product is identified as perillyl alcohol by boiling point, refractive index, and by nuclear magnetic resonance data, as set forth below.

The boiling point of the product is 56°–60°C at 0.07 mm (literature 107°–110°C at 12.5 mm). The refractive index at 20°C is 1.50117 (literature 1.50054 for the laevo-rotatory form).

The nmr data obtained on a Varian A-60 instrument are as follows: (60MHz) (CCl$_4$) δ1.5-2.5 (broad m, 10H), δ3.87 (singlet, 2H, CH$_2$ $_{OH}$), δ4.68 singlet, 2H,

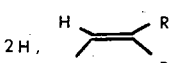

δ5.64(broad m, 1H, 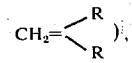 ).

EXAMPLES 3–9

The catalyst may comprise a ferrous/ferric system, although a cuprous/cupric system is considerably more δ 1.6-2.5 (broad m, 11H) , δ 3.88 (broad m, 1H, 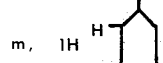 , δ 4.66 (singlet, 2H, 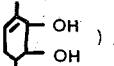 ) , δ 5.45 (broad m, 1H 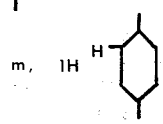 ) .

effective, as shown in Table I below, wherein the present yields are compared as a result of employing the process described in Example 2.

TABLE I

| Example No. | Ratio Beta-Pinene to Benzoyl Peroxide | Catalysts | % Yield |
|---|---|---|---|
| 3 | 2:1 | FeBr$_2$/ferric benzoate | 34.2 |
| 4 | 2:1 | FeBr$_2$/ferric acetate | 38.1 |
| 5 | 2:1 | FeCl$_2$/ferric benzoate | 38.1 |
| 6 | 2:1 | FeCl$_2$/ferric acetate | 31.6 |
| 7 | 2:1 | CuBr/cupric benzoate | 60.5 |
| 8 | 2:1 | CuBr/cupric acetate | 59.2 |
| 9 | 2:1 | CuCl/cupric acetate | 67.1 |

EXAMPLE 10

Yield of perillyl alcohol is improved by employing a 1:1 benzene-acetic acid solvent instead of acetonitrile; by employing a cupric compound in addition to a cuprous compound as the catalyst system; and by increasng the ratio of beta-pinene to benzoyl peroxide, as shown in Table II below. The process used to obtain the data is the same as that described in Example 2.

TABLE II

| Col. No. 1 | 2 | 3 | 4 | 5 |
|---|---|---|---|---|
| | Percent Yield | | | |
| Ratio Beta-Pinene to Benzoyl Peroxide | Benzene-Acetic Acid (1:1) Solvent CuCl catalyst | Benzene-Acetic Acid (1:1) Solvent CuCl-Cupric Benzoate catalyst | Acetonitrile Solvent CuCl-Catalyst | Acetonitrile Solvent CuCl-Cupric Benzoate Catalyst |
| 1:1 | 36.9 | 56.0 | 30.3 | 51.3 |
| 2:1 | 50.6 | 73.6 | 46.0 | 66.5 |
| 3:1 | 65.1 | 71.7 | 55.3 | 61.2 |
| 4:1 | 65.1 | 74.7 | 57.2 | 64.5 |
| 5:1 | 74.3 | 77.5 | 62.5 | 64.5 |

A comparison of columns 2 and 3 and 4 and 5 shows the advantage of using a cupric compound in conjunction with a cuprous catalyst; columns 2 and 4 and 3 and 5 show the advantage of a 1:1 benzene-acetic acid over acetonitrile as a solvent; and an inspection of each vertical column of yield percentages shows the advantages of using the higher ratios of beta-pinene to benzoyl peroxide. The use of large excesses of beta-pinene adds little to the cost of the final product, since the unreacted beta-pinene is readily recoverable by distillation under vacuum before the step of hydrolyzing the benzoate.

EXAMPLE 11

Perillyl alcohol enhances the lavandin note in the following perfume blend which is useful in detergent compositions:

| | Percent By Weight |
|---|---|
| Terpineol | 20.0 |
| Anethole | 1.0 |
| Lavandin oil | 20.0 |
| Perillyl alcohol | 5.0 |
| Phenylethyl alcohol | 2.0 |
| Diphenyl oxide | 1.0 |
| Linalool | 20.0 |
| Lemongrass oil | 1.0 |
| Lemon Terpenes | 30.0 |
| | 100.0 |

EXAMPLE 12

Perillyl alcohol imparts a lavandin note in the following perfume blend.

| | Percent by Weight |
|---|---|
| Linalool | 30 |
| Linalyl acetate | 25 |
| Camphor | 8 |
| Cineole | 7 |
| Perillyl alcohol | 10 |
| d-Limonene | 10 |
| Methyl benzyl ketone | 3 |
| Borneol | 3 |
| Terpinyl Acetate | 4 |
| | 100 |

EXAMPLE 13

Perillyl alcohol enhances the lavandin note of the following blend:

| | Percent by Weight Preferred | Range |
|---|---|---|
| Linalool | 32 | 20–50 |
| Linalyl acetate | 27 | 20–50 |
| d-Limonene | 11 | 10–20 |
| Perillyl alcohol | 30 | 0.5–30 |
| | 100 | |

EXAMPLE 14

The following coriander perfume blend is an example of the utility of trans-carveol as a perfume ingredient.

| | Percent by Weight |
|---|---|
| Linalool | 40 |
| Trans-carveol | 10 |
| d-Limonene | 20 |
| Carvone | 20 |
| Anethole | 10 |
| | 100 |

EXAMPLE 15

Addition of trans-carveol to Clary Sage oil enhances the top note, as in the following blend.

| | Percent by Weight |
|---|---|
| Clary Sage oil | 60 |
| Trans-carveol | 20 |
| Linalool | 10 |
| Carvone | 10 |
| | 100 |

EXAMPLE 16

Trans-carveol imparts a herbaceous, balsamic, spice note in the following perfume blend.

|  | Percent by Weight |
| --- | --- |
| Trans-carveol | 10 |
| Eugenol | 22 |
| Allyl ionone | 2 |
| Coumarin | 15 |
| Amyl salicylate | 23 |
| Linalyl acetate | 22 |
| 6-Methyl coumarin | 1 |
| Isobutyl salicylate | 5 |
|  | 100 |

EXAMPLE 17

Trans-carveol enhances the lavandin character in the following blend:

|  | Percent by Weight |
| --- | --- |
| Terpineol | 20.0 |
| Anethole | 1.0 |
| Lavandin oil | 20.0 |
| Trans-carveol | 5.0 |
| Phenylethyl alcohol | 2.0 |
| Diphenyl oxide | 1.0 |
| Linalool | 20.0 |
| Lemongrass oil | 1.0 |
| Lemon terpenes | 30.0 |
|  | 100.0 |

EXAMPLE 18

Trans-carveol enhances the spice note of the following perfume mixture:

|  | Percent by Weight Preferred | Range |
| --- | --- | --- |
| Linalyl acetate | 23 | 20–50 |
| Eugenol | 23 | 20–50 |
| Amyl salicylate | 24 | 20–50 |
| Trans-carveol | 30 | 0.5–30 |
|  | 100 |  |

Having thus described the invention, and having set forth the best modes for the practice thereof, modifications and variations within the scope of the invention will occur to those skilled in the art, and the scope of the invention is to be limited only by the appended claims.

What is claimed is:

1. A process for preparing a cycloaliphatic monoterpenic alcohol selected from the group consisting of trans-carveol and perillyl alcohol comprising the steps of
   i. preparing a mixture of
      a. an isomeric pinene selected from the group consisting of alpha-pinene and beta-pinene,
      b. a cuprous salt selected from the group consisting of cuprous chloride and cuprous bromide,
      c. a polar solvent selected from the group consisting of acetonitrile and a 1:1 benzene:acetic acid mixture, and
      d. benzoyl peroxide,
   said pinene being in molar excess with relation to said benzoyl peroxide in a ratio of from about 1:1 to about 5:1, said cuprous salt being in a catalaytic amount,
   ii. heating said mixture at a temprature of about 40°C to about 85°C, whereby a benzoate ester is formed,
   iii. hydrolyzing said ester in an alkaline aqueous alcoholic medium, thereby forming said cycloaliphatic monoterpenic alcohol,
   iv. recovering said cycloaliphatic monoterpenic alcohol.

2. A process in accordance with claim 1, wherein said benzoyl peroxide is incorporated into said mixture incrementally.

3. A process in accordance with claim 1 for preparing a cycloaliphatic monoterpenic alcohol selected from the group consisting of trans-carveol and perillyl alcohol comprising the steps of
   i. preparing a mixture of
      a. an isomeric pinene selected from the group consisting of alpha-pinene and beta-pinene,
      b. a cuprous salt selected from the group consisting of cuprous chloride and cuprous bromide,
      c. a cupric salt selected from the group consisting of cupric benzoate and cupric acetate,
      d. a polar solvent selected from the group consisting of acetonitrile and a 1:1 benzene:acetic acid mixture, and
      e. benzoyl peroxide,
   said pinene being in molar excess with relation to said benzoyl peroxide in a ratio of from about 1:1 to about 5:1, said cuprous salt being in catalytic amount, and said cupric salt being in an amount at least sufficient to minimize polymerization,
   ii. heating said mixture at a temperature of about 40°C to about 85°C, whereby a benzoate ester is formed,
   iii. hydrolyzing said ester in an alkaline aqueous alcoholic medium, thereby forming said cycloaliphatic monoterpenic alcohol,
   iv. recovering said cycloaliphatic monoterpenic alcohol.

4. A process in accordance with claim 3 wherein the cuprous catalyst is present from about 0.05 grams to about 5 grams per 100 ml of solvent and the cupric polymerization inhibitor is present from about 0.5 grams to about 10 grams per 100 ml of solvent.

5. A process in accordance with claim 3 wherein the mixture is heated at a temperature of from about 50°C to about 75°C.

* * * * *